(12) United States Patent
Bertsche

(10) Patent No.: US 6,487,274 B2
(45) Date of Patent: Nov. 26, 2002

(54) X-RAY TARGET ASSEMBLY AND RADIATION THERAPY SYSTEMS AND METHODS

(75) Inventor: Kirk Joseph Bertsche, San Jose, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 09/772,435

(22) Filed: Jan. 29, 2001

(65) Prior Publication Data

US 2002/0101958 A1 Aug. 1, 2002

(51) Int. Cl.[7] .............................................. H01J 35/10
(52) U.S. Cl. ...................... 378/143; 378/65; 378/98.9; 378/124; 378/144
(58) Field of Search ................. 378/98.9, 124, 378/143, 144, 65, 98.11

(56) References Cited

U.S. PATENT DOCUMENTS

| | | | | |
|---|---|---|---|---|
| 2,942,126 A | * | 6/1960 | Silbermann | 378/109 |
| 3,610,984 A | * | 10/1971 | Seki et al. | 378/125 |
| 4,029,963 A | | 6/1977 | Alvarez et al. | 378/5 |
| 4,132,917 A | | 1/1979 | Bildstein et al. | 378/144 |
| 4,158,770 A | * | 6/1979 | Davis, Jr. et al. | 378/2 |
| 4,247,774 A | | 1/1981 | Brooks | 250/367 |
| 4,445,226 A | | 4/1984 | Brody | 378/98.9 |
| 4,484,341 A | | 11/1984 | Luniewski | 378/69 |
| 4,712,226 A | * | 12/1987 | Horbaschek | 378/134 |
| 4,736,398 A | | 4/1988 | Graeff et al. | 378/8.3 |
| 4,945,552 A | | 7/1990 | Ueda et al. | 378/98.11 |
| 4,998,268 A | * | 3/1991 | Winter | 378/63 |
| 5,003,571 A | * | 3/1991 | Kido et al. | 378/98.11 |
| 5,065,419 A | * | 11/1991 | Leguen et al. | 378/125 |
| 5,396,530 A | | 3/1995 | Tsutsui et al. | 378/98.11 |
| 5,396,889 A | * | 3/1995 | Ueda et al. | 600/407 |
| 5,511,105 A | * | 4/1996 | Knott | 378/134 |
| 5,537,452 A | | 7/1996 | Shepherd et al. | 378/65 |
| 5,748,700 A | | 5/1998 | Shepherd et al. | 378/65 |
| 5,754,622 A | * | 5/1998 | Hughes | 378/65 |
| 5,757,885 A | | 5/1998 | Yao et al. | 378/130 |
| 5,778,045 A | | 7/1998 | von Stetten et al. | 378/98.9 |
| 5,815,547 A | | 9/1998 | Shepherd et al. | 378/65 |
| 5,825,848 A | | 10/1998 | Virshup et al. | 378/144 |
| 5,841,832 A | | 11/1998 | Mazess et al. | 378/56 |
| 5,894,503 A | | 4/1999 | Shpherd et al. | 378/203 |
| 5,907,592 A | * | 5/1999 | Levinson | 378/4 |
| 6,001,054 A | * | 12/1999 | Regulla et al. | 600/1 |
| 6,104,779 A | | 8/2000 | Shepherd et al. | 378/65 |
| 6,118,853 A | | 9/2000 | Hansen et al. | 378/143 |

OTHER PUBLICATIONS

O.Z. Ostapiak et al., "Megavoltage imaging with low Z targets: Implementation and characterization of an investigational system," Med. Phys., 25 (10), 1910–1918 (Oct. 1998).

* cited by examiner

*Primary Examiner*—David P. Porta
*Assistant Examiner*—Allen C. Ho

(57) ABSTRACT

A multi-region target that is configured to selectively generate two different energy distributions when exposed to an excitation electron beam is described. The multi-region target includes multiple regions with different x-ray generating characteristics. Thus, the interaction between an excitation electron beam and the target generates an x-ray beam with an energy distribution that depends upon which target region is exposed to the excitation electron beam. The different x-ray spectra may be used to produce an enhanced contrast x-ray image. A method of detecting the rotational position of the multi-region target based upon the contrast level of the resulting images also is described.

22 Claims, 4 Drawing Sheets

X-RAY TARGET ASSEMBLY AND RADIATION THERAPY SYSTEMS AND METHODS

TECHNICAL FIELD

This invention relates to x-ray target assemblies and radiation therapy systems and methods.

BACKGROUND

Radiation therapy involves delivering a high, curative dose of radiation to a tumor, while minimizing the dose delivered to surrounding healthy tissues and adjacent healthy organs. Therapeutic radiation doses may be supplied by a charged particle accelerator that is configured to generate a high-energy (e.g., several MeV) electron beam. The electron beam may be applied directly to one or more therapy sites on a patient, or it may be used to generate a photon (e.g., X-ray) beam, which is applied to the patient. An x-ray tube also may supply therapeutic photon radiation doses to a patient by directing a beam of electrons from a cathode to an anode formed from an x-ray generating material composition. The shape of the radiation beam at the therapy site may be controlled by discrete collimators of various shapes and sizes or by multiple leaves (or finger projections) of a multi-leaf collimator that are positioned to block selected portions of the radiation beam. The multiple leaves may be programmed to contain the radiation beam within the boundaries of the therapy site and, thereby, prevent healthy tissues and organs located beyond the boundaries of the therapy site from being exposed to the radiation beam.

X-ray bremsstrahlung radiation typically is produced by directing a charged particle beam (e.g., an electron beam) onto a solid target. X-rays are produced from the interaction between fast moving electrons and the atomic structure of the target. The intensity of x-ray radiation produced is a function of the atomic number of the x-ray generating material. In general, materials with a relatively high atomic number (i.e., so-called "high Z" materials) are more efficient producers of x-ray radiation than materials having relatively low atomic numbers (i.e., "low Z" materials). However, many high Z materials have low melting points, making them generally unsuitable for use in an x-ray target assembly where a significant quantity of heat typically is generated by the x-ray generation process. Many low Z materials have good heat-handling characteristics, but are less efficient producers of x-ray radiation. Tungsten typically is used as an x-ray generating material because it has a relatively high atomic number (Z=74) and a relatively high melting point (3370° C.).

The bremsstrahlung process produces x-rays within a broad, relatively uniform energy spectrum. Subsequent transmission of x-rays through an x-ray target material allows different x-ray energies to be absorbed preferentially. The high-Z targets typically used for multi-MeV radiation therapy systems produce virtually no low energy x-rays (below around 100 keV). The resultant high energy x-rays (mostly above 1 MeV) are very penetrating, a feature that is ideal for therapeutic treatment. In fact, in treatment applications, it is desirable not to have a significant amount of low energy x-rays in the treatment beam, as low-energy beams tend to cause surface burns at the high doses needed for therapy.

Before and/or after a dose of therapeutic radiation is delivered to a patient, a diagnostic x-ray image of the area to be treated typically is desired for verification and archiving purposes. The x-ray energies used for therapeutic treatment, however, typically are too high to provide high quality diagnostic images because high-energy therapeutic beams tend to pass through bone and tissue with little attenuation. As a result, very little structural contrast is captured in such images. In general, the x-ray energies that are useful for diagnostic imaging are around 100 keV and lower. High-Z targets produce virtually no x-rays in this diagnostic range. Low-Z targets (e.g., targets with atomic numbers of 30 or lower, such as aluminum, beryllium, carbon, and aluminum oxide targets), on the other hand, produce x-ray spectra that contain a fraction of low-energy x-rays that are in the 100 keV range and, therefore, are suitable for diagnostic imaging applications. See, for example, O. Z. Ostapiak et al., "Megavoltage imaging with low Z targets: implementation and characterization of an investigational system," Med. Phys., 25 (10), 1910–1918 (October 1998). Because of the need for verification and documentation of therapeutic treatments, "portal films" or "portal images" typically are taken in real time (or nearly real time) using the high-energy x-ray treatment beam (see, e.g., U.S. Pat. Nos. 5,686,733, 4,995,068 and 5,138,647). If the images are collected electronically, various image enhancement techniques may be employed to enhance contrast and general quality (see, e.g., U.S. Pat. Nos. 5,675,624 and 6,148,060). One way to improve image quality is to use a separate low-energy diagnostic x-ray source. This source may produce a beam that is separated from the high-energy treatment beam and may be aimed in the opposite direction through the patient (see, e.g., U.S. Pat. No. 5,233,990). Alternatively, the diagnostic beam may be directed through the collimation system of the treatment beam (see, e.g., U.S. Pat. Nos. 5,471,516 and 6,134,295). In another approach, separate diagnostic and therapy devices are used, with careful registration and restriction of patient motion as the patient is transferred between each device (see, e.g., U.S. Pat. No. 5,851,182).

For sub-MeV diagnostic x-ray systems (as opposed to the multi-megavolt systems typically used for therapy), x-ray absorption edges advantageously may be used to enhance images. For example, dual-energy x-ray techniques may be used to separate bony tissue from soft tissue in medical imaging. Typically, the two distinct energy bands are selected to be above and below an absorption edge of the object to be imaged. By subtracting the image data produced with the higher energy x-ray radiation from the image data produced with the lower energy x-ray radiation, an enhanced contrast image may be obtained.

Many different dual-energy x-ray schemes have been proposed. In a switched mode dual-energy x-ray system, the voltage of an x-ray tube periodically is changed from a high voltage to a low voltage to shift the energy spectra of the resulting x-ray beams. A broadband detector collects image data produced by the two different x-ray radiation spectra. In an alternative approach, a broadband (or polychromatic) x-ray beam may illuminate an object, and a dual band detector may be used to collect image data at two different x-ray radiation energy bands. Typically, a front detector measures total x-ray flux and a rear detector measures high energy x-rays that pass through an intervening filter. High contrast x-ray images may be obtained from these two measurements. Still other dual energy x-ray imaging schemes have been proposed.

SUMMARY

The invention features a multi-region target that is configured to selectively generate two different energy distributions when exposed to an excitation electron beam. In particular, the inventive multi-region target includes multiple regions with different x-ray generating characteristics. Thus, the interaction between an excitation electron beam and the target generates an x-ray beam with an energy distribution that depends upon which target region is exposed to the excitation electron beam. The different x-ray spectra may be used to produce an enhanced contrast x-ray image. The invention also features a novel method of detecting the rotational position of the multi-region target based upon the contrast level of the resulting images.

In one aspect, the invention features a target assembly comprising a multi-region target having an exposed surface, a first region and a second region, and a cooling mechanism coupled to the first and second regions of the target. The first region comprises a first x-ray generating characteristic. The second region is laterally displaced from the first region with respect to an excitation beam incident upon the exposed surface and comprises a second x-ray generating characteristic that is different from the first x-ray generating characteristic.

Embodiments in accordance with this aspect of the invention may include one or more of the following features.

The first region preferably comprises a first x-ray generating material composition, and the second region preferably comprises a second x-ray generating material composition that is different from the first material composition. The first x-ray generating material composition preferably includes a material with a relatively high atomic number, and the second x-ray generating material composition preferably includes a material with a relatively low atomic number. The relatively high atomic number material may have an atomic number of 72 or higher, and the relatively low atomic number material may have an atomic number of 30 or lower. The relatively high atomic number material may be tungsten or tantalum or gold, and the relatively low atomic number material may be aluminum, beryllium, carbon or aluminum oxide.

In some embodiments, the first region is larger than the second region. The target may be substantially disk-shaped. The first and second regions may correspond to respective sectors of the substantially disk-shaped target. Alternatively, the second region may correspond to one or more peripheral portions of the substantially disk-shaped target, and the first region may correspond to remaining portions of the substantially disk-shaped target. In this case, the target assembly may be shifted laterally so that the electron beam strikes only the first region or strikes both regions as the target rotates.

The cooling mechanism may include a target holder configured to support the target for rotation and to expose the target to a cooling fluid stream, whereby the target rotates about an axis of rotation upon exposure to the cooling fluid stream.

In another aspect, the invention features a radiation therapy system comprising a source of an electron beam, and the above-described multi-region target positioned to intercept the electron beam.

Embodiments in accordance with this aspect of the invention may include one or more of the following features.

The radiation therapy system may include a computer configured to identify images produced from x-rays generated by the first target region and to identify images produced from x-rays generated by the second target region. The computer may be configured to identify images based upon image contrast. The computer may be configured to produce an enhanced image by combining image data produced from x-rays generated by the second target region with image data produced from x-rays generated by the first target region.

In another aspect, the invention features a radiation therapy method in accordance with which an electron beam is generated and the above-described multi-region target is positioned to intercept the electron beam.

Embodiments in accordance with this aspect of the invention may include one or more of the following features.

Images preferably are generated from x-rays generated by exposing the target to the electron beam. Images produced from x-rays generated by the first target region may be identified, and images produced from x-rays generated by the second target region may be identified. Images may be identified based upon image contrast. An enhanced image may be produced by combining image data produced from x-rays generated by the second target region with image data produced from x-rays generated by the first target region.

Among the advantages of the invention are the following.

The invention provides both a low-Z target to provide high-quality diagnostic images and a high-Z target to provide the bulk of the therapeutic treatment. Because much of the treatment dose is delivered with beam from the high-Z target, damage to skin and surface tissue is less than would be obtained from a low-Z target alone. In addition, the high-Z and low-Z targets may be interchanged rapidly, reducing the risk that an anatomical structure (e.g., surface tissue or internal organ) will move between the two exposure modes. This feature also enables two different exposure images to be combined to enhance image contrast by removing high-energy x-ray noise (or image degradation) from the resultant image. By applying the proper gain to a high-Z image and combining this data with image data obtained with the low-Z target, any noise or image artifacts due to the high energy x-rays (which are present with both targets) may be subtracted away, leaving the image that would have been obtained from a beam solely composed of lower-energy x-rays. In effect, this artificially synthesizes a low-energy x-ray spectrum with little high-energy x-ray content.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Figure 1:
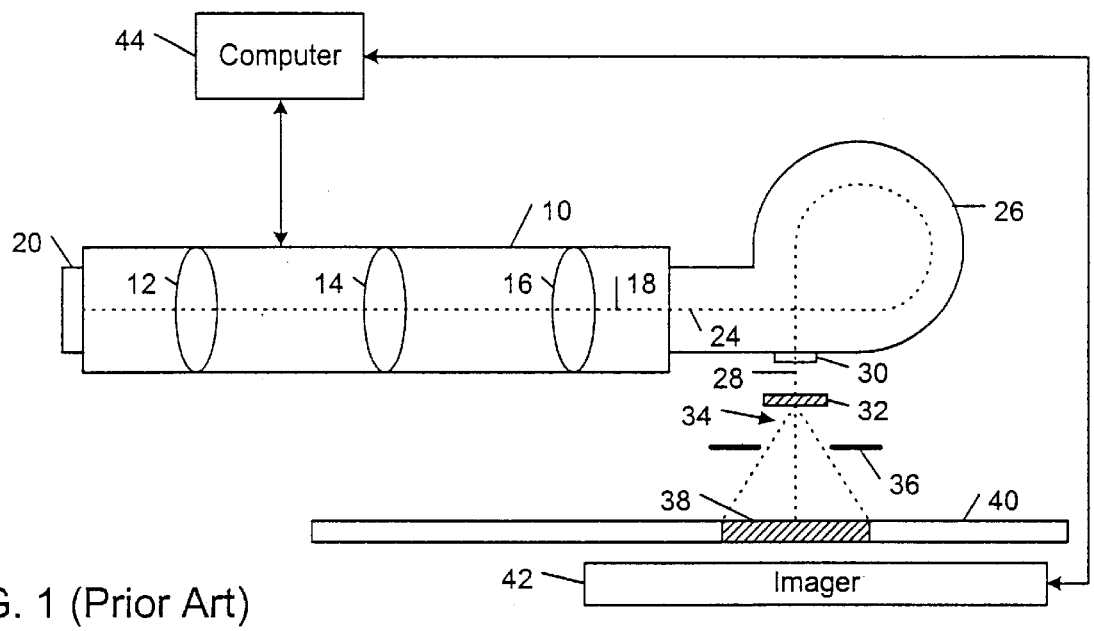
FIG. 1 is a block diagram of a radiation treatment device delivering a therapeutic radiation beam to a therapy site on a patient.

Referring to FIG. 1, in one embodiment, a charged particle accelerator 10 for use in a medical radiotherapy device includes a series of accelerating cavities 12, 14, 16 that are aligned along a beam axis 18. A particle source 20 (e.g., an electron gun) directs charged particles (e.g., electrons) into accelerating cavity 12. As the charged particles travel through the succession of accelerating cavities 12–16, the particles are focused and accelerated by an electromagnetic field that is applied by an external source. The resulting accelerated particle beam 24 may be directed to a magnetic energy filter 26 that bends beam 24 by approximately 270°. A filtered output beam 28 is directed through a window 30 to a target 32 that generates an x-ray beam 34. The intensity of radiation beam 34 typically is constant. One or more adjustable leaves 36 may be positioned to block selected portions of radiation beam 34 to conform the boundary of radiation beam 34 to the boundaries of a therapy site 38 on a patient 40. An imager 42 collects image data corresponding to the intensity of radiation passing through patient 40. A computer 44 typically is programmed to control the operation of leaves 36 to generate a prescribed intensity profile over the course of a treatment, and to control the operation of imager 42.

As explained in detail below, target 32 is configured to selectively produce from output beam 28 x-ray beams 34 with two different energy distributions. In particular, target 32 includes multiple regions with different x-ray generating characteristics. Thus, the interaction between output electron beam 28 and target 32 generates an x-ray beam 34 with an energy distribution that depends upon which target region is exposed to the electron beam 28. As explained in detail below, the different x-ray energy distributions may be used to produce an enhanced contrast x-ray image.

Figure 2B:
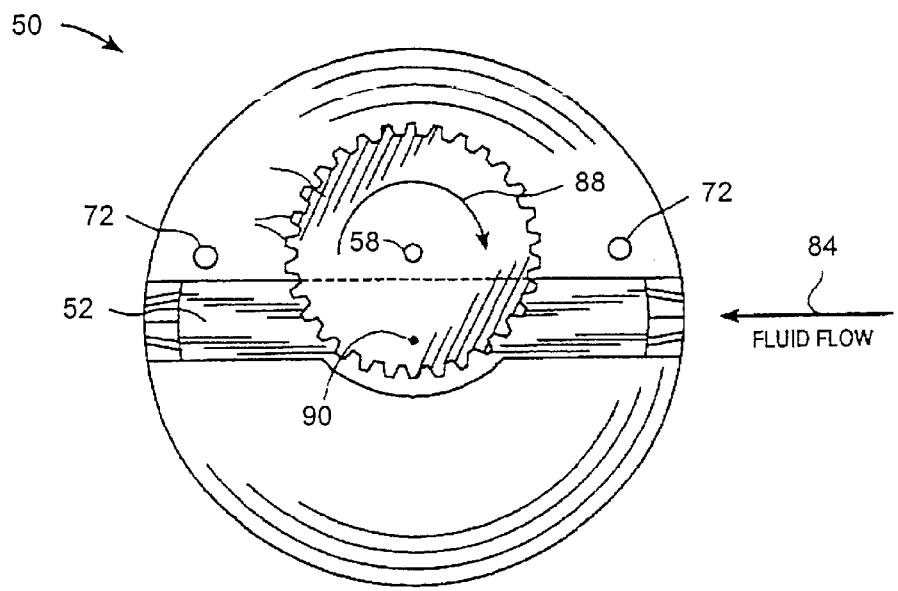
FIG. 2B is a diagrammatic top view of the x-ray target assembly of FIG. 2A and a cooling fluid stream rotating an x-ray target mounted within the target assembly.
Figure 2A:
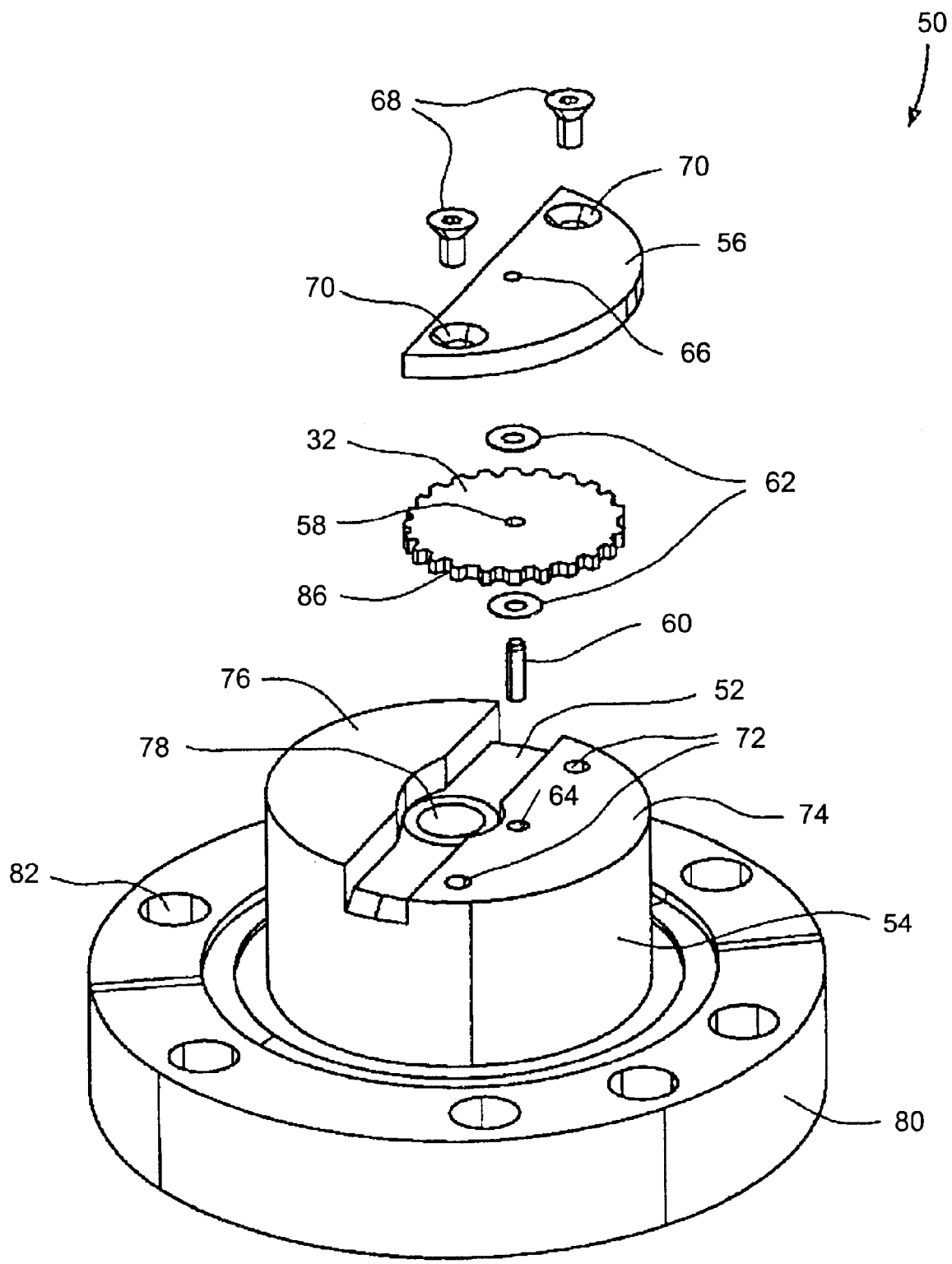
FIG. 2A is a diagrammatic exploded view of an x-ray target assembly.

As shown in FIG. 2B, in operation, a fluid 84 (e.g., water) may be directed through fluid channel 52. The flowing fluid 84 engages a plurality of notches 86 in target 32, causing target 32 to rotate in a direction indicated by arrow 88. Output electron beam 28 may be focused as a spot 90 on an exposed surface of target 32. Because the target is rotating and the electron beam spot 90 is fixed, the electron beam spot 90 traverses over the exposed surface of target 32 along a circular path. The circular distribution of the beam spot 90 spreads the heat generated from the beam around the target, thereby reducing the heat flux at any one point on target 32. The rotation of target 32 also allows localized target areas that are exposed to output electron beam 28 to cool before being re-exposed to output electron beam 28. In operation, cooling fluid 84 flows continuously over rotating target 32 to further cool target 32.

Additional details regarding the construction and operation of target assembly 50 may be found in U.S. Pat. No. 5,757,885, which is incorporated herein by reference.

Figure 3:
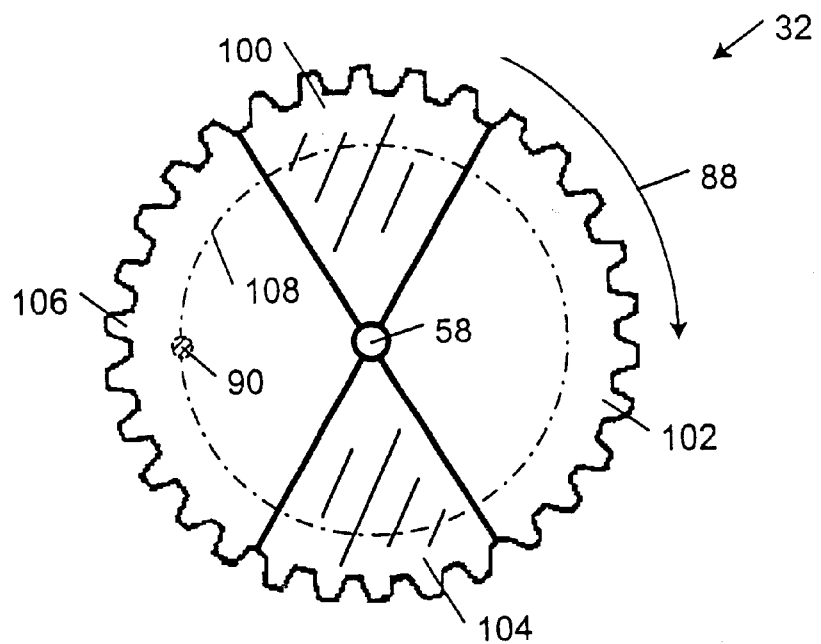
FIG. 3 is a diagrammatic top view of a multi-region target and an excitation electron beam traversing a circular path across an exposed target surface as the target rotates.

Referring to FIG. 3, in one embodiment, target 32 includes four regions 100, 102, 104, 106 that correspond to respective sectors of the substantially disk-shaped target 32. Regions 100, 104 are formed from an x-ray generating material composition that is different from the x-ray generating material composition of regions 102, 106. Regions 100, 104 preferably include a material composition with a relatively low atomic number (e.g., an atomic number of thirty or less, such as aluminum, beryllium, carbon and alloys or compounds thereof), whereas regions 102, 106 preferably include a material composition with a relatively high atomic number (e.g., an atomic number of seventy-two or greater, such as tungsten, tantalum, gold and alloys thereof). Thus, exposure of regions 100, 104 to output electron beam 28 produces x-ray radiation that contains a fraction of low-energy x-rays, and exposure of regions 102, 106 to output electron beam 28 produces x-ray radiation with essentially no low-energy x-rays. In operation, as target 32 rotates, output electron beam spot 90 traverses a circular path 108 across the exposed surface of target 32 to produce a sequence of high energy x-ray beams which alternately include and do not include some low-energy x-rays.

Figure 4:
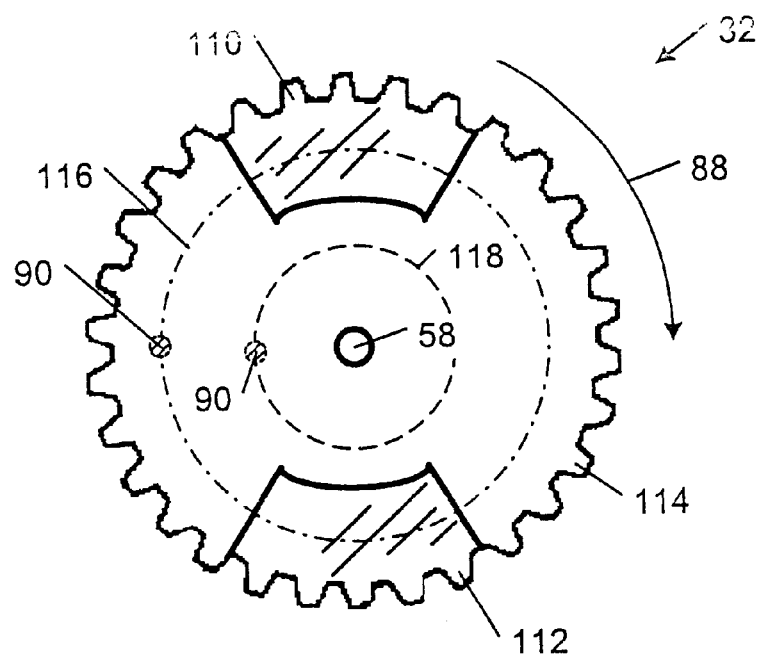
FIG. 4 is a diagrammatic top view of another multi-region target and two excitation electron beams traversing respective circular paths across an exposed target surface as the target rotates.

Referring to FIG. 4, in another embodiment, target 32 includes two regions 110, 112 that correspond to peripheral portions of the substantially disk-shaped target 32, and a region 114 that corresponds to remaining portions of the substantially disk-shaped target 32. Regions 110, 112 are formed from an x-ray generating material composition that is different from the x-ray generating material composition of region 114. Regions 110, 112 preferably include a material composition with a relatively low atomic number (e.g., an atomic number of thirty or less, such as aluminum, beryllium, carbon and alloys or compounds thereof), whereas region 114 preferably includes a material composition with a relatively high atomic number (e.g., an atomic number of seventy-two or greater, such as tungsten, tantalum, gold and alloys thereof). Thus, exposure of regions 110, 112 to output electron beam 28 produces x-ray radiation that contains a fraction of low-energy x-rays, and exposure of region 114 to output electron beam 28 produces x-ray radiation that contains essentially no low-energy x-rays. In operation, as target 32 rotates, output electron beam spot 90 may traverse a circular path 116 across the exposed surface of target 32 to produce a sequence of high energy x-ray beams which alternately include and do not include some low-energy x-rays. Alternatively, output electron beam spot 90 may traverse a circular path 118 across the exposed surface of target 32 to produce a uniform sequence of relatively high-energy x-ray beams containing essentially no low-energy x-rays.

The different regions of the target embodiments of FIGS. 3 and 4 may be formed from uniform pieces of metal that fit together to form a relatively thin disk with peripheral notches. The metal pieces may be clamped or brazed together to form an integrated unitary target. Alternatively, the respective material compositions of the different target regions may be deposited by conventional deposition techniques onto a substrate (e.g., a graphite-based substrate) that serves as a support for the different x-ray generating material compositions and as a cooling mechanism for dissipating heat generated at the target regions exposed to output electron beam 28. The target embodiments also may be formed by other conventional target formation processes.

As shown in FIGS. 3 and 4, the low Z material regions 100, 104 (FIG. 3) and 110, 112 (FIG. 4) are smaller in area than the corresponding high Z material regions 102, 106 (FIG. 3) and 114 (FIG. 4). Accordingly, the electron beam spot paths over the low Z regions are shorter than the electron beam spot paths over the high Z regions. By this design, the dose of highly absorbing low energy x-rays delivered to the patient may be reduced. In other embodiments, the low Z material regions and the high Z material regions may have the same surface area, but computer 44 may be programmed to gate the charged particle accelerator 10 on and off as a function of target position. In this way, the number of electron beam pulses incident upon the low Z material regions may be controlled to achieve a desired level of patient exposure to the highly absorbing low energy x-rays generated from the low Z material regions or to achieve a desired image contrast level.

Computer 44 may determine the position of target 32 relative to output electron beam 28 in a variety of different ways. For example, a conventional optical, mechanical or magnetic angular position sensor may be located at the target to monitor the rotational position of the target. Alternatively, computer 44 may be programmed to determine which material region was exposed to the output electron beam 28 to produce a particular image frame based upon the contrast of the image frame. In particular, when the contrast of an image frame is greater than a threshold contrast value, computer 44 identifies the image frame as having a low-energy (or low Z) image frame; when the contrast of an image frame is less than the threshold contrast value, computer 44 identifies the image frame as a high-energy (or high Z) image frame. As used herein, "contrast" refers to the range of difference between the lightest and darkest values of a picture, or maximum and minimum brightness values. Computer 44 also may utilize one or more of these position sensing techniques to monitor the rotational rate of target 32.

Figure 5:
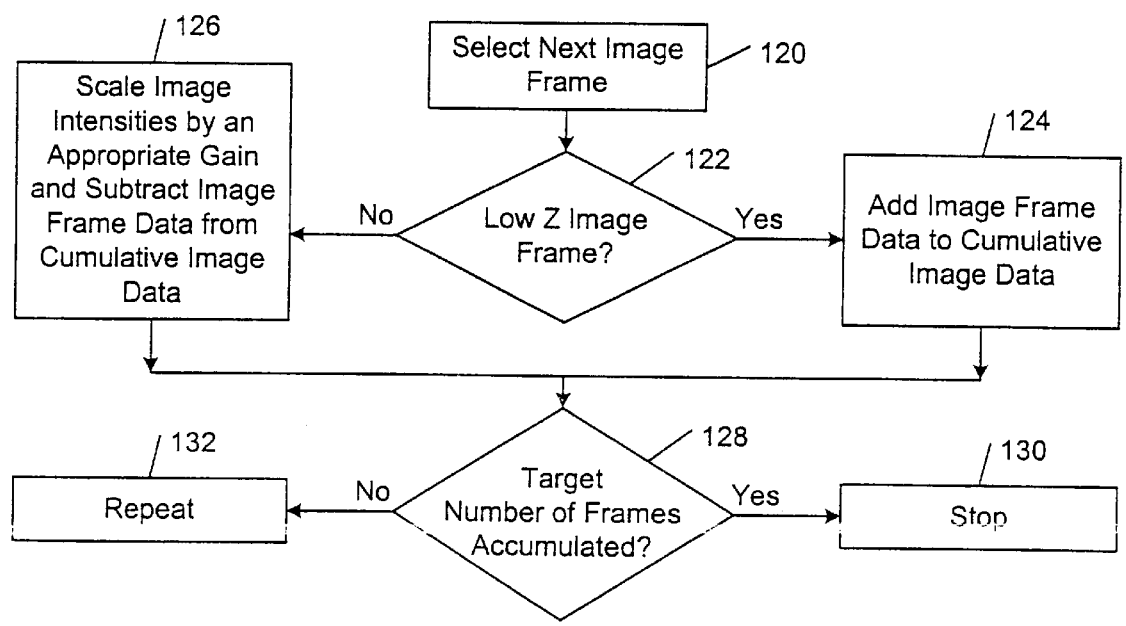
FIG. 5 is a flow diagram of a method of accumulating x-ray image frames to produce an enhanced contrast x-ray image.

Referring to FIG. 5, in one embodiment, computer 44 may utilize the different x-ray energy distributions generated by the above-described multi-region target to produce an enhanced contrast x-ray image as follows. Computer 44 selects an image frame captured by imager 42 (step 120). The image frame may correspond to a single pulse of output electron beam 28 or to a series of beam pulses incident upon the same target region. If the image frame corresponds to a low Z image frame (step 122), computer 44 adds the image frame data to a cumulate image data file (step 124). If the image frame corresponds to a high Z image frame (step 122), computer 44 scales image intensities by an appropriate gain factor and subtracts the image frame data from the cumulate image data file (step 126). Computer 44 may identify high Z and low Z image frames based upon information received from a rotational position sensor or based upon the contrast level of the image frames, as described above. If the target number of image frames has been accumulated (step 128), computer 44 stops the image data accumulation process (step 130). Otherwise, computer 44 repeats the process (step 132) by selecting the next image frame to be accumulated (step 120). With appropriate scaling of the subtracted images, the effects of the high-energy x-rays (which are generated by both targets but are not useful for diagnostic imaging) may be subtracted. The resulting image has an enhanced contrast, corresponding to a spectrum of predominantly low-energy x-rays. In addition, because target 32 may rotate at a relatively high rate (e.g., up to 10,000 rpm), the effects of any patient movement during imaging may be reduced.

Other embodiments are within the scope of the claims. For example, although the target embodiments of FIGS. 3 and 4 are described in connection with a cooling fluid-based target assembly, other target assembly designs also may be used. In these embodiments, the targets may be in the form of disks that are free of peripheral notches. In other embodiments, the targets may oscillate back-and-forth, rather than rotate, in which case the targets may have a non-disk shape. In some other embodiments, the different x-ray generating characteristics of the different regions of target 32 may be achieved by varying the thicknesses of selected regions of a target with a uniform material composition, rather than varying the material compositions of the different regions. In addition, other target embodiments may include any number of different-Z regions to provide a desired number of different x-ray radiation distributions with the same target.

Still other embodiments are within the scope of the claims.

What is claimed is:

1. A target assembly, comprising:
   a target having
      a surface exposed to receive an excitation beam along an expected beam path including at least first and second non-overlapping beam path portions,
      a first region operable to generate substantial x-radiation characterized by a first energy distribution in response to an excitation beam incident upon the exposed surface along the first beam path portion, and
      a second region operable to generate substantial x-radiation characterized by a second energy distribution different from the first energy distribution in response to an excitation beam incident upon the exposed surface along the second beam path portion; and
   a cooling mechanism coupled to the first and second regions of the target.

2. The target assembly of claim 1, wherein the first region comprises a first x-ray generating material composition, and the second region comprises a second x-ray generating material composition that is different from the first material composition.

3. The target assembly of claim 2, wherein the first x-ray generating material composition is characterized by a higher atomic number than the second x-ray generating material composition.

4. The target assembly of claim 3, wherein the first x-ray generating material composition includes a material with an atomic number of 72 or higher, and the second x-ray generating material composition includes a material with an atomic number of 30 or lower.

5. The target assembly of claim 3, wherein the relatively high atomic number material is tungsten or tantalum or gold, and the relatively low atomic number material is aluminum, beryllium, carbon or aluminum oxide.

6. The target assembly of claim 3, wherein the first region is larger than the second region.

7. The target assembly of claim 1, wherein the target is substantially disk-shaped and the first and second regions correspond to respective sectors of the substantially disk-shaped target.

8. The target assembly of claim 1, wherein the target is substantially disk-shaped, the second region corresponds to one or more peripheral portions of the substantially disk-shaped target, and the first region corresponds to remaining portions of the substantially disk-shaped target.

9. A target assembly, comprising:
   a target having
      an exposed surface,
      a first region comprising a first x-ray generating characteristic, and
      a second region laterally displaced from the first region with respect to an excitation beam incident upon the exposed surface and comprising a second x-ray generating characteristic that is different from the first x-ray generating characteristic; and
   a cooling mechanism coupled to the first and second regions of the target, wherein the cooling mechanism includes a target holder configured to support the target for rotation and to expose the target to a cooling fluid stream, whereby the target rotates about an axis of rotation upon exposure to the cooling fluid stream.

10. A radiation therapy system, comprising:

a source of an electron beam; and a target positioned to intercept the electron beam and having
  a surface exposed to receive an excitation beam along an expected beam path including at least first and second non-overlapping beam path portions,
  a first region operable to generate substantial x-radiation characterized by a first energy distribution in response to an excitation beam incident upon the exposed surface along the first beam path portion, and
  a second region operable to generate substantial x-radiation characterized by a second energy distribution different from the first energy distribution in response to an excitation beam incident upon the exposed surface along the second beam path portion.

11. The target assembly of claim 10, wherein the first region comprises a first x-ray generating material composition, and the second region comprises a second x-ray generating material composition that is different from the first material composition.

12. The radiation therapy system of claim 11, wherein the first x-ray generating material composition is characterized by a higher atomic number than the second x-ray generating material composition.

13. The radiation therapy system of claim 12, wherein the first region is larger than the second region.

14. The radiation therapy system of claim 10, further comprising a computer configured to identify images produced from x-rays generated by the first target region and to identify images produced from x-rays generated by the second target region.

15. The radiation therapy system of claim 10, wherein the source is configured to produce an electron beam with an energy of 1 MeV or greater.

16. A radiation therapy system, comprising:

a source of an electron beam;

a target positioned to intercept the electron beam and having an exposed surface, a first region comprising a first x-ray generating characteristic, and a second region laterally displaced from the first region with respect to an electron beam incident upon the exposed surface and comprising a second x-ray generating characteristic that is different from the first x-ray generating characteristic; and a computer configured to identify images produced from x-rays generated by the first target region and to identify images produced from x-rays generated by the second target region, wherein the computer is configured to identify images based upon image contrast.

17. The radiation therapy system of claim 16, wherein the computer is configured to produce an enhanced image by combining image data produced from x-rays generated by the second target region with image data produced from x-rays generated by the first target region.

18. A radiation therapy method, comprising:

generating an electron beam; and positioning to intercept the electron beam a target having
  a surface exposed to receive an excitation beam along an expected beam path including at least first and second non-overlapping beam path portions,
  a first region operable to generate substantial x-radiation characterized by a first energy distribution in response to an excitation beam incident upon the exposed surface along the first beam path portion, and
  a second region operable to generate substantial x-radiation characterized by a second energy distribution different from the first energy distribution in response to an excitation beam incident upon the exposed surface along the second beam path portion.

19. The radiation therapy method of claim 18, further comprising:

generating images from x-rays generated by exposing the target to the electron beam;

identifying images produced from x-rays generated by the first target region; and identifying images produced from x-rays generated by the second target region.

20. The radiation therapy method of claim 18, further comprising producing an enhanced image by combining image data produced from x-rays generated by the second target region with image data produced from x-rays generated by the first target region.

21. The radiation therapy method of claim 18, wherein an electron beam of 1 MeV or greater is produced.

22. A radiation therapy method, comprising:

generating an electron beam;

positioning to intercept the electron beam a target having an exposed surface, a first region comprising a first x-ray generating characteristic, and a second region laterally displaced from the first region with respect to an electron beam incident upon the exposed surface and comprising a second x-ray generating characteristic that is different from the first x-ray generating characteristic;

generating images from x-rays generated by exposing the target to the electron beam;

identifying images produced from x-rays generated by the first target region; and identifying images produced from x-rays generated by the second target region, wherein images are identified based upon image contrast.

* * * * *